(12) United States Patent
Chandanson et al.

(10) Patent No.: US 11,457,967 B2
(45) Date of Patent: Oct. 4, 2022

(54) DRIVER INSTRUMENTS AND RELATED METHODS

(71) Applicant: Medos International Sàrl, Le Locle (CH)

(72) Inventors: Thibault Chandanson, Villers le lac (FR); Richard W. Fournier, New Bedford, MA (US); Shawn D. Stad, Raynham, MA (US); Frank Spratt, Middleboro, MA (US); Sam Grossman, Providence, RI (US); Henri Defossez, Neuchatel (CH); Renaud Rouge, Le Locle (CH); Philip A. Cormier, Quincy, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 154 days.

(21) Appl. No.: 16/120,206

(22) Filed: Aug. 31, 2018

(65) Prior Publication Data

US 2019/0059967 A1 Feb. 28, 2019

Related U.S. Application Data

(63) Continuation of application No. 14/685,454, filed on Apr. 13, 2015, now Pat. No. 10,085,786.

(51) Int. Cl.
*A61B 17/70* (2006.01)
*A61B 17/88* (2006.01)
(Continued)

(52) U.S. Cl.
CPC ...... *A61B 17/8875* (2013.01); *A61B 17/7082* (2013.01); *B25B 23/0035* (2013.01);
(Continued)

(58) Field of Classification Search
CPC ............ A61B 17/8872; A61B 17/8875; A61B 17/888; A61B 17/8888; A61B 17/8891;
(Continued)

(56) References Cited

U.S. PATENT DOCUMENTS 5,431,660 A 7/1995 Burke
5,573,530 A 11/1996 Fleury et al.
(Continued)

FOREIGN PATENT DOCUMENTS

DE 86 21 556 U1 10/1986
DE 88 15 530 U1 2/1989
(Continued)

OTHER PUBLICATIONS

U.S. Appl. No. 14/685,484, filed Apr. 13, 2015, Driver Instruments and Related Methods.
(Continued)

*Primary Examiner* — Kevin T Truong
*Assistant Examiner* — Tracy L Kamikawa
(74) *Attorney, Agent, or Firm* — Barnes & Thornburg LLP

(57) ABSTRACT

Driver instruments are disclosed herein with various features for improving usability, easing the task of cleaning or sterilizing the instrument, reducing patient trauma associated with use of the instrument, and/or reducing the cost and assembly burden of the instrument. For example, a driver instrument can include a guide sleeve to protect patient tissue from damage caused by rotating components of the instrument or a bone anchor assembly coupled thereto, and to protect extension tabs of the bone anchor assembly from inadvertent separation. By way of further example, an instrument can include a preload assembly for maintaining engagement of a driver shaft of the instrument with a bone anchor assembly. As yet another example, an instrument can (Continued)

consist of a small number of components which are configured for simple, tool-free assembly and disassembly. An instrument can also be configured for use with bone anchor assemblies with and without extension tabs.

25 Claims, 8 Drawing Sheets

(51) Int. Cl.
  *B25B 23/00* (2006.01)
  *A61B 17/00* (2006.01)
  *A61B 17/16* (2006.01)
(52) U.S. Cl.
  CPC ....... *A61B 17/1655* (2013.01); *A61B 17/7098* (2013.01); *A61B 17/8816* (2013.01); *A61B 2017/0046* (2013.01)
(58) Field of Classification Search
  CPC ............ A61B 17/8894; A61B 17/7076; A61B 17/708; A61B 17/7082; A61B 17/1655; A61B 17/7098; A61B 17/8816; A61B 2017/0046; A61B 2017/925; A61B 2017/928; B25B 23/0035
  See application file for complete search history.

(56) References Cited

U.S. PATENT DOCUMENTS

| | | |
|---|---|---|
| 5,645,546 A | 7/1997 | Fard |
| 5,741,268 A | 4/1998 | Schutz |
| 5,941,885 A | 8/1999 | Jackson |
| 5,996,452 A * | 12/1999 | Chiang ................ B25B 15/001 279/157 |
| 6,155,143 A | 12/2000 | Wu |
| 6,189,422 B1 | 2/2001 | Stihl |
| 6,258,090 B1 | 7/2001 | Jackson |
| 6,415,693 B1 | 7/2002 | Simon et al. |
| 6,723,100 B2 | 4/2004 | Biedermann et al. |
| 6,736,820 B2 | 5/2004 | Biedermann et al. |
| 6,854,742 B2 | 2/2005 | Salyer et al. |
| 6,974,460 B2 | 12/2005 | Carbone et al. |
| 7,179,261 B2 | 2/2007 | Sicvol et al. |
| 7,326,198 B2 | 2/2008 | Desarzens et al. |
| 7,367,979 B2 | 5/2008 | Abdelgany |
| 7,491,208 B2 | 2/2009 | Pond, Jr. et al. |
| 7,575,581 B2 | 8/2009 | Lovell |
| 7,771,430 B2 | 8/2010 | Jones et al. |
| 7,966,914 B2 | 6/2011 | Abdelgany |
| 7,972,364 B2 | 7/2011 | Biedermann et al. |
| 8,070,751 B2 | 12/2011 | Justis et al. |
| 8,087,329 B2 | 1/2012 | Schumacher et al. |
| 8,096,996 B2 | 1/2012 | Gutierrez et al. |
| 8,100,916 B2 * | 1/2012 | Kumar ................ A61B 17/7082 606/104 |
| 8,100,951 B2 | 1/2012 | Justis et al. |
| 8,273,089 B2 | 9/2012 | Jackson |
| 8,323,286 B2 | 12/2012 | Justis |
| 8,394,108 B2 | 3/2013 | McLean et al. |
| 8,439,922 B1 | 5/2013 | Arnold et al. |
| 8,460,307 B2 * | 6/2013 | Saidha ................ A61B 17/7035 606/104 |
| 8,460,308 B2 | 6/2013 | Marino et al. |
| 8,486,084 B2 | 7/2013 | Huene |
| 8,603,094 B2 | 12/2013 | Walker et al. |
| 8,636,740 B2 | 1/2014 | Weaver et al. |
| 8,814,880 B2 | 8/2014 | McAllister et al. |
| 8,845,649 B2 | 9/2014 | Jackson |
| 8,974,494 B2 | 3/2015 | Paulk et al. |
| 9,220,542 B2 | 12/2015 | Kerboul et al. |
| 10,085,786 B2 | 10/2018 | Chandanson et al. |
| 10,441,326 B2 | 10/2019 | DiVincenzo et al. |
| 10,653,457 B2 | 5/2020 | Erramilli et al. |
| 2004/0158247 A1 | 8/2004 | Sitiso et al. |
| 2006/0089651 A1 | 4/2006 | Trudeau et al. |
| 2006/0178673 A1 | 8/2006 | Curran |
| 2006/0184174 A1 | 8/2006 | Harris, Jr. et al. |
| 2007/0043378 A1 | 2/2007 | Kumar et al. |
| 2007/0106283 A1 | 5/2007 | Garcia et al. |
| 2008/0045970 A1 | 2/2008 | Saidha et al. |
| 2009/0221877 A1 | 9/2009 | Woods |
| 2009/0234395 A1 | 9/2009 | Hoffman et al. |
| 2009/0255383 A1 | 10/2009 | Hsieh |
| 2009/0275994 A1 * | 11/2009 | Phan ................ B25B 13/488 606/86 A |
| 2010/0114174 A1 | 5/2010 | Jones et al. |
| 2010/0298838 A1 | 11/2010 | Walters |
| 2011/0288599 A1 | 11/2011 | Michielli et al. |
| 2012/0109208 A1 | 5/2012 | Justis et al. |
| 2012/0197263 A1 | 8/2012 | Copf et al. |
| 2012/0203288 A1 * | 8/2012 | Lange ................ A61B 17/7082 606/305 |
| 2012/0253402 A1 | 10/2012 | McLean |
| 2013/0053901 A1 | 2/2013 | Cormier et al. |
| 2013/0096618 A1 | 4/2013 | Chandanson et al. |
| 2013/0103039 A1 | 4/2013 | Hopkins et al. |
| 2013/0282019 A1 | 10/2013 | Bouliane |
| 2014/0031873 A1 | 1/2014 | Jackson |
| 2014/0100583 A1 | 4/2014 | Butler et al. |
| 2014/0107708 A1 * | 4/2014 | Biedermann .......... A61B 90/94 606/278 |
| 2014/0276894 A1 * | 9/2014 | Ramsay ............. A61B 17/7076 606/104 |
| 2014/0324062 A1 * | 10/2014 | Heuer .................. B25B 23/101 606/104 |
| 2015/0066089 A1 * | 3/2015 | Nelson ................ A61B 17/7085 606/265 |
| 2015/0201987 A1 * | 7/2015 | Lemoine ............. A61B 17/8891 606/104 |
| 2015/0359572 A1 | 12/2015 | Reimels et al. |
| 2015/0374418 A1 | 12/2015 | Martin |
| 2016/0030100 A1 | 2/2016 | DiVincenzo et al. |
| 2016/0296266 A1 | 10/2016 | Chandanson et al. |
| 2017/0181776 A1 | 6/2017 | Beretta et al. |
| 2018/0177536 A1 | 6/2018 | DiVincenzo et al. |
| 2018/0214190 A1 | 8/2018 | Erramilli et al. |
| 2020/0038072 A1 | 2/2020 | DiVincenzo et al. |
| 2020/0237412 A1 | 7/2020 | Erramilli et al. |

FOREIGN PATENT DOCUMENTS

| | | |
|---|---|---|
| DE | 198 49 564 A1 | 2/2000 |
| DE | 20 2013 004369 U1 | 7/2014 |
| WO | 2014091454 A1 | 6/2014 |

OTHER PUBLICATIONS

Invitation to Pay Additional Fees/Partial International Search for Application No. PCT/US2016/027069, dated Jun. 20, 2016 (8 pages).
International Search Report and Written Opinion for Application No. PCT/US2016/027069; dated Sep. 9, 2016 (8 pages).
International Preliminary Report on Patentability for Application No. PCT/US2016/027069; dated Oct. 26, 2017 (13 pages).
[NoAuthorListed] Expedium Verse® Spinal System, System Guide, 2015, 52 pages.
Extended European Search Report for Application No. 17882928.9, dated Aug. 17, 2020 (9 pages).
International Search Report and Written Opinion for Application No. PCT/US17/62689, dated Feb. 22, 2018 (9 Pages).

* cited by examiner

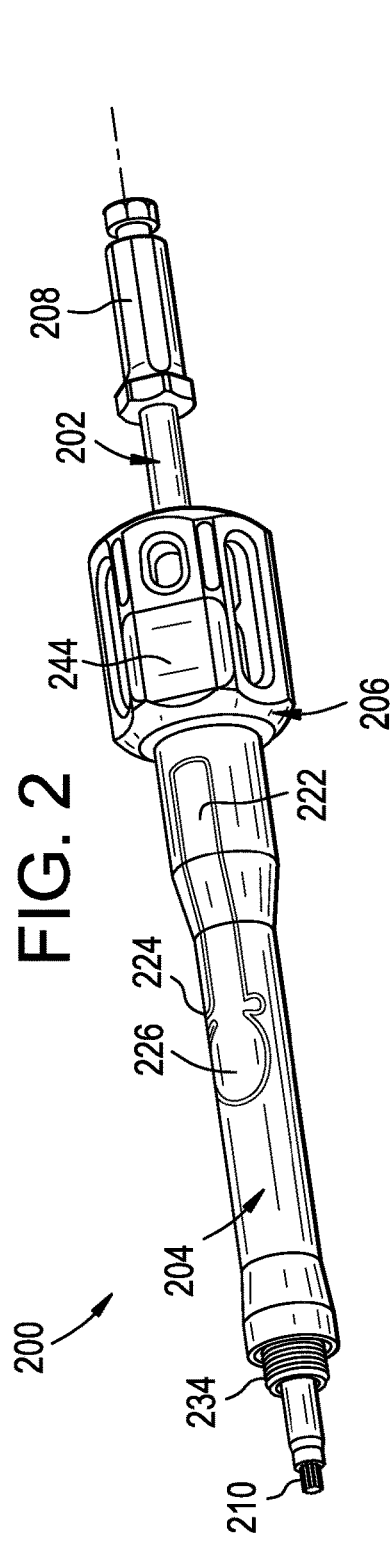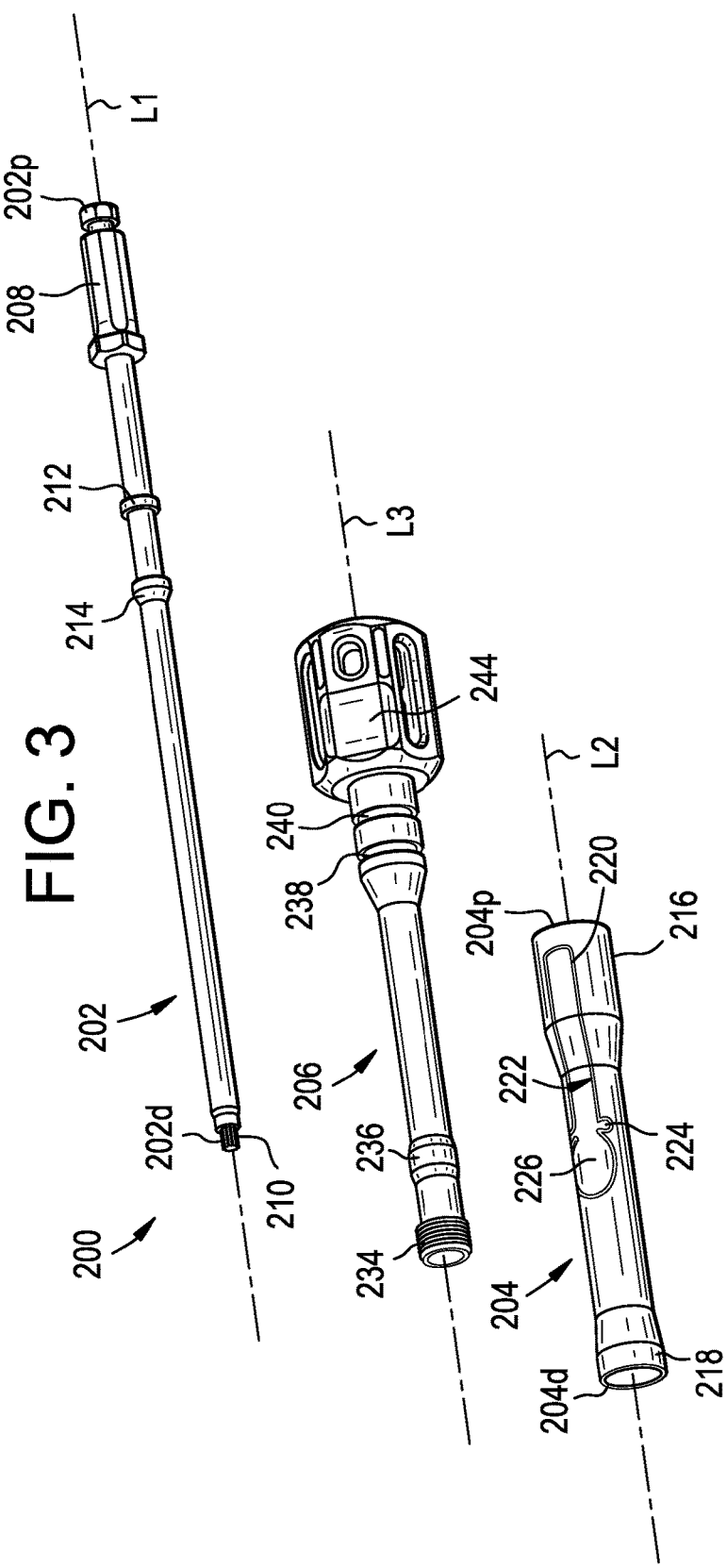

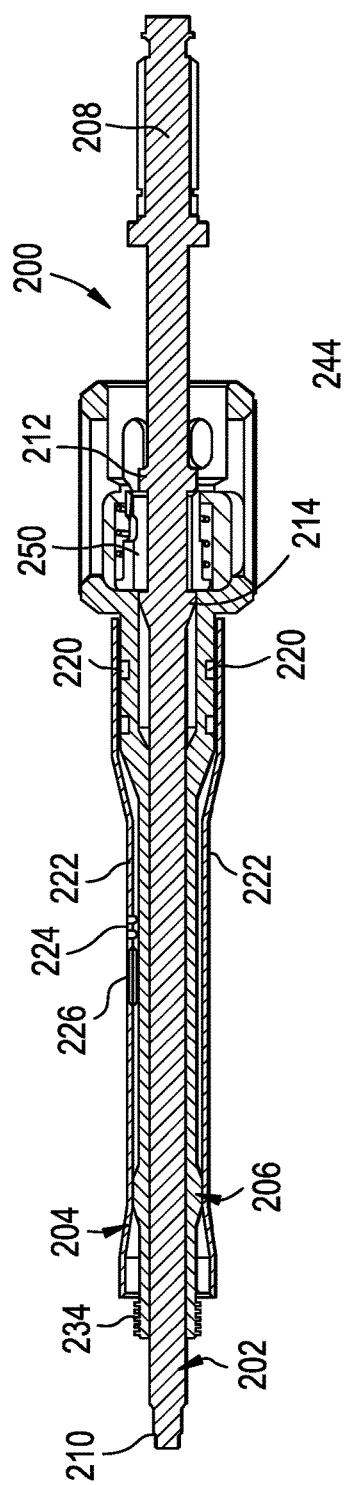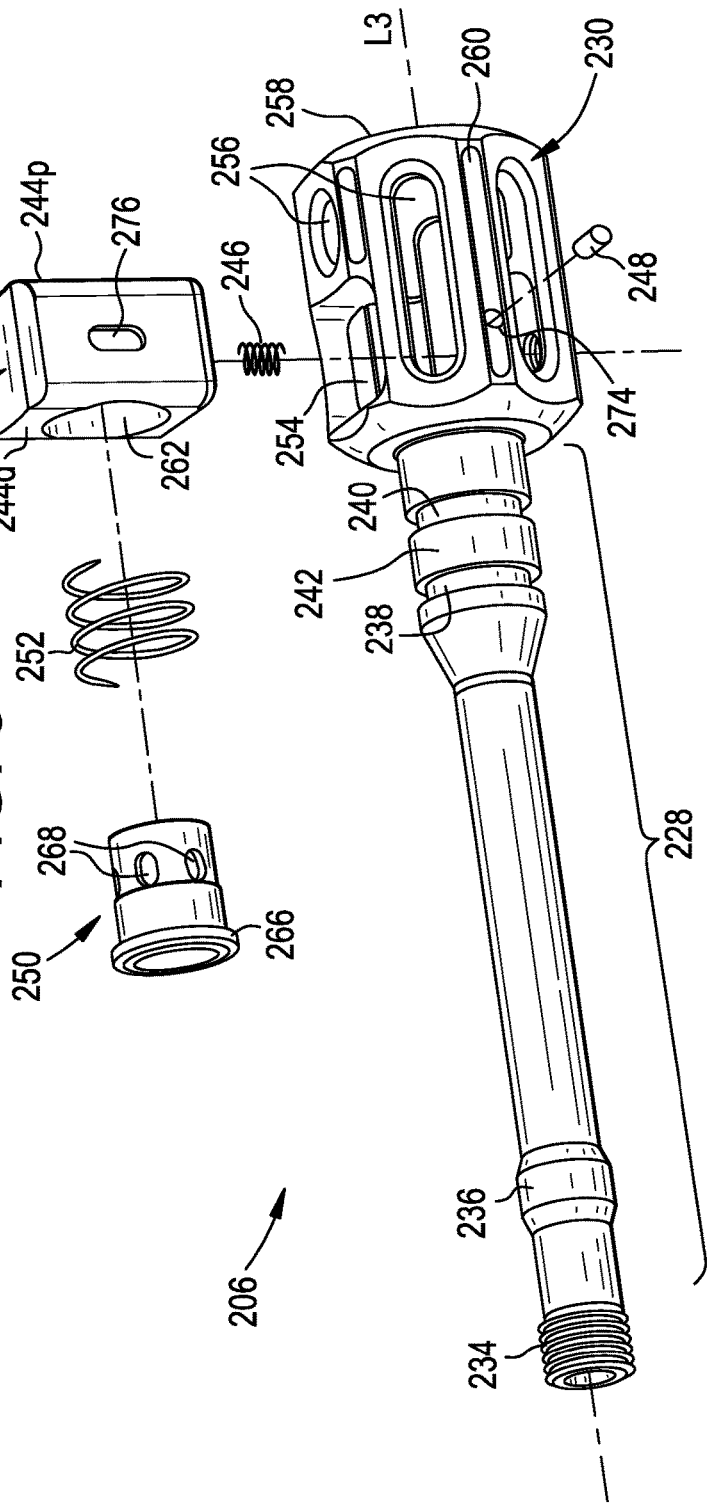

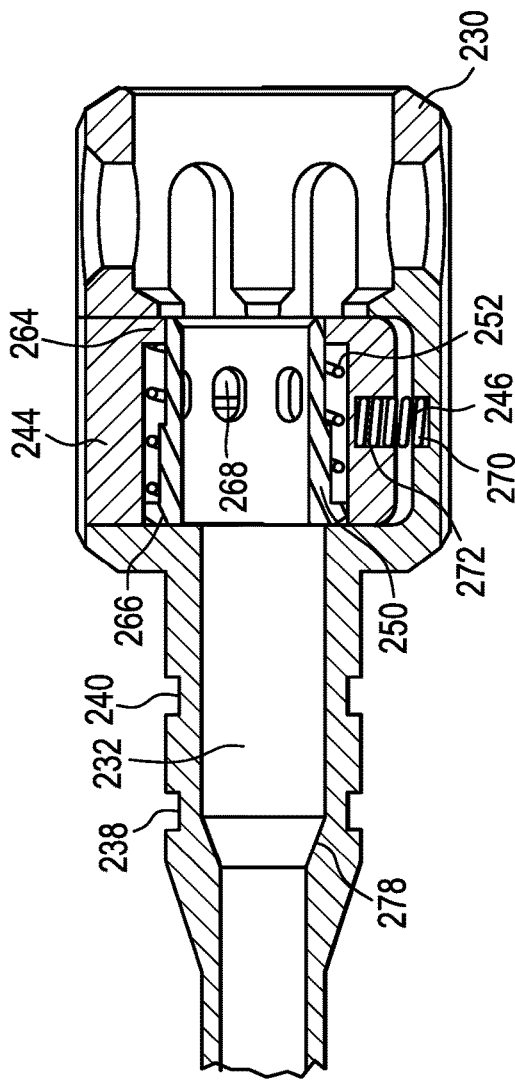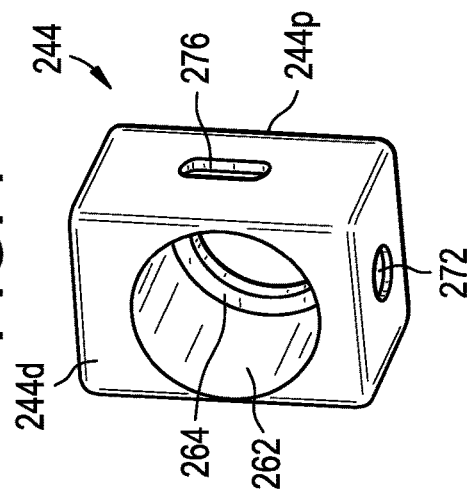

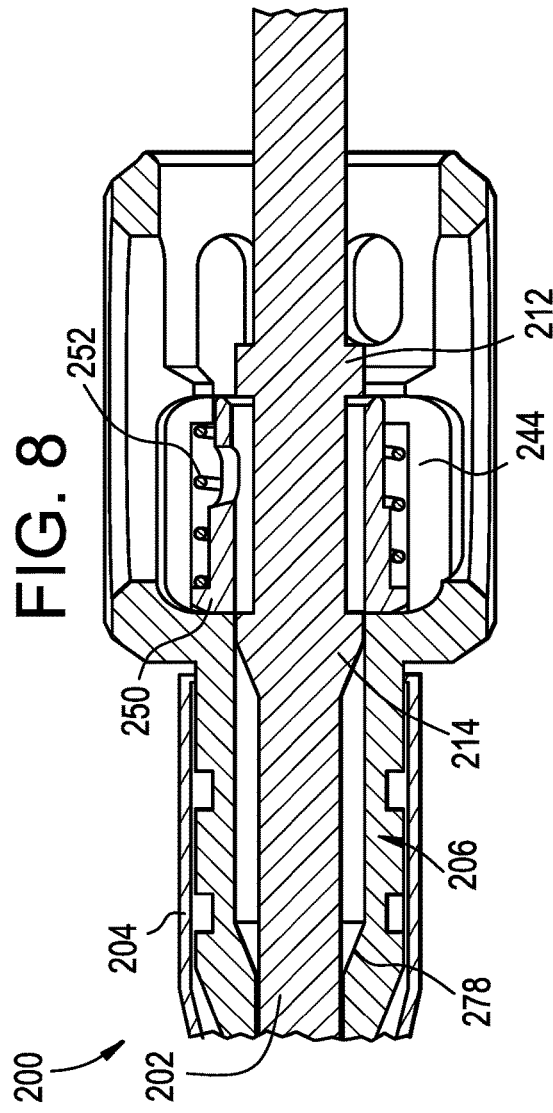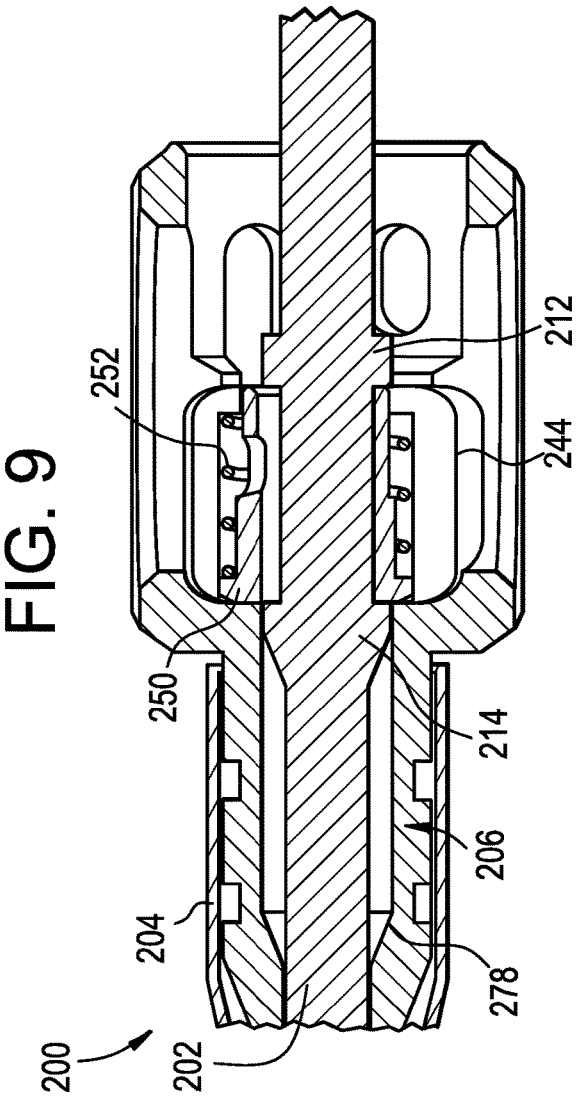

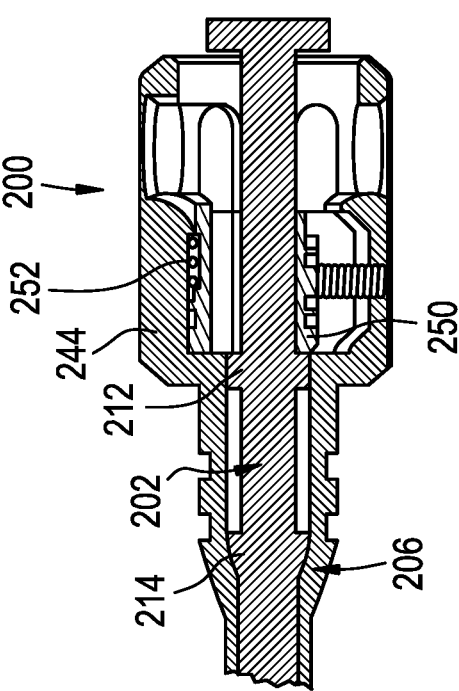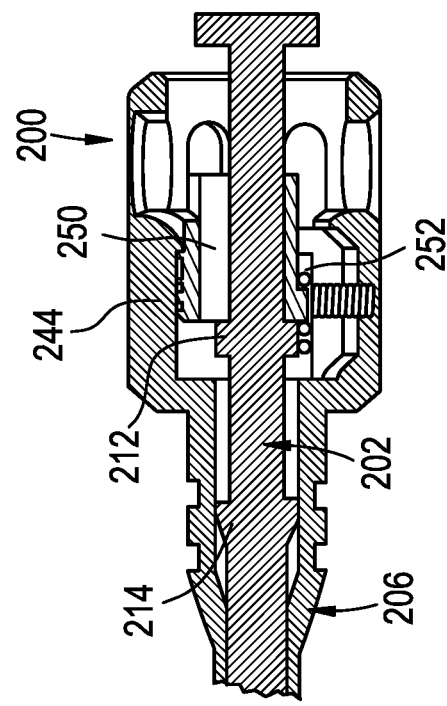

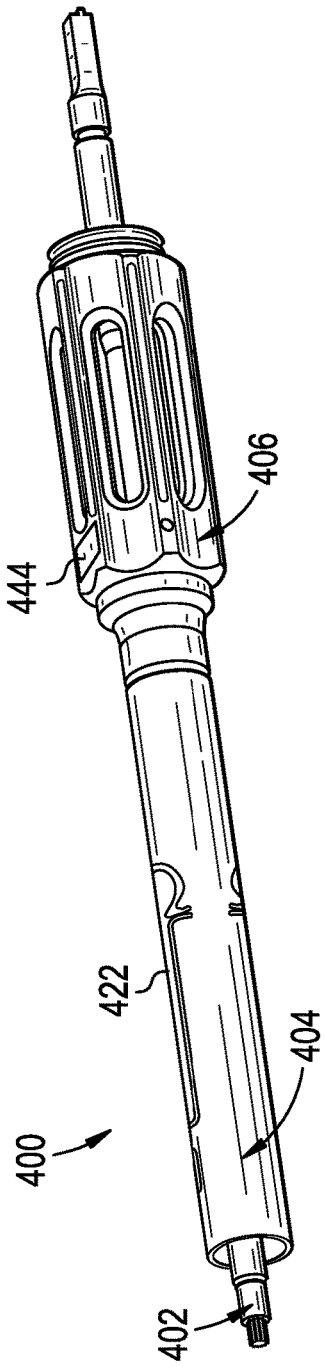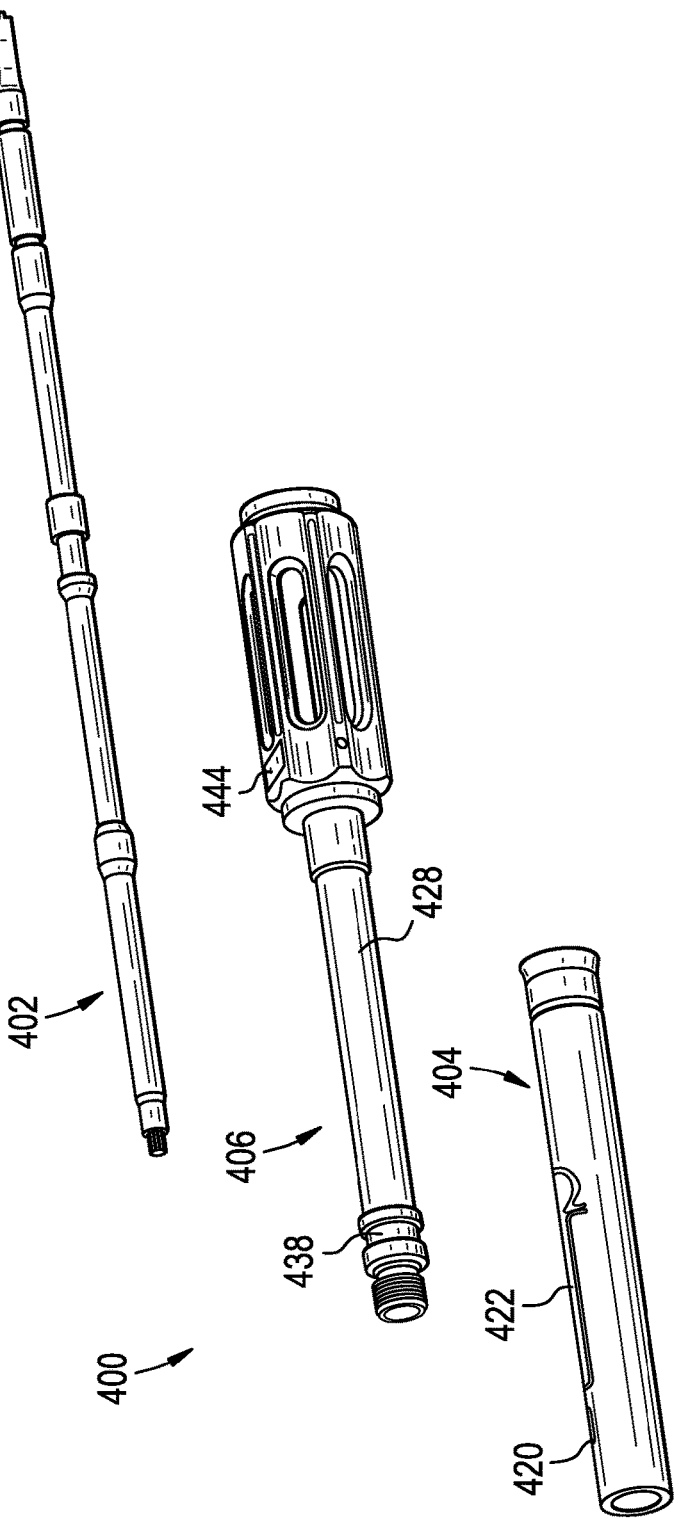

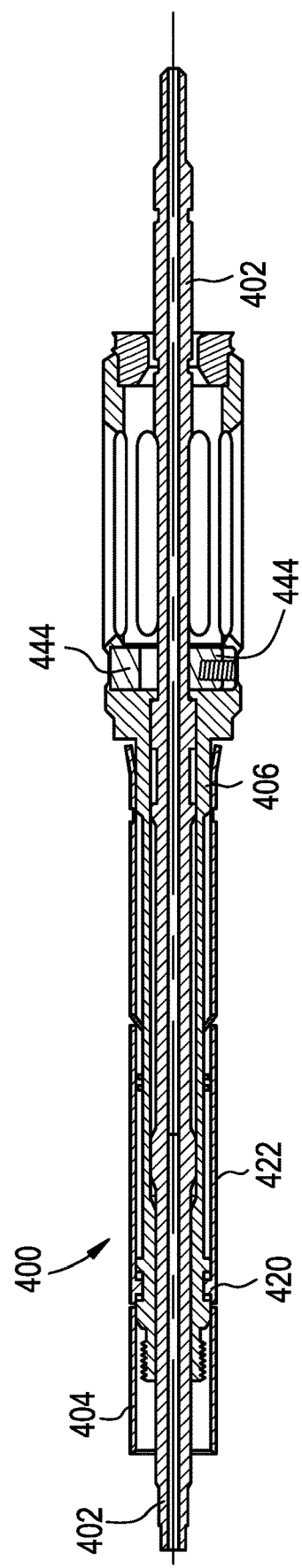

DRIVER INSTRUMENTS AND RELATED METHODS

CROSS-REFERENCE TO RELATED APPLICATIONS

This application is a continuation of U.S. patent application Ser. No. 14/685,454, filed Apr. 13, 2015, and entitled "Driver Instruments and Related Methods." This application is hereby incorporated by reference in its entirety.

FIELD

Driver instruments and related methods for driving bone anchor assemblies into bone are disclosed herein.

BACKGROUND

Bone anchors can be used in orthopedic surgery to fix bone during healing, fusion, or other processes. In spinal surgery, for example, bone anchors can be used to secure a spinal fixation element to one or more vertebrae to rigidly or dynamically stabilize the spine.

In a conventional procedure for coupling a bone anchor to bone, access to the bone is obtained, for example by forming a skin incision and resecting soft tissue disposed over the bone or by using a minimally-invasive technique. A guidewire is partially inserted into the bone to establish the trajectory for the bone anchor. The bone anchor is then advanced over the guidewire and rotationally driven into the bone using a driver instrument. The guidewire is then removed and one or more fixation elements are coupled to the bone anchor.

While a number of driver instruments have been developed for advancing bone anchors into bone, there is a continual need for improved driver instruments and related methods of driving bone anchors.

SUMMARY

Driver instruments are disclosed herein with various features for improving usability, easing the task of cleaning or sterilizing the instrument, reducing patient trauma associated with use of the instrument, and/or reducing the cost and assembly burden of the instrument. For example, a driver instrument can include a guide sleeve to protect patient tissue from damage caused by rotating components of the instrument or a bone anchor assembly coupled thereto, and to protect extension tabs of the bone anchor assembly from inadvertent separation. By way of further example, an instrument can include a preload assembly for maintaining engagement of a driver shaft of the instrument with a bone anchor assembly. As yet another example, an instrument can consist of a small number of components which are configured for simple, tool-free assembly and disassembly. An instrument can also be configured for use with bone anchor assemblies with and without extension tabs.

In some embodiments, an instrument for driving a bone anchor assembly into bone includes a driver shaft having a distal drive tip and a proximal driven end; an elongate body having proximal and distal ends that defines a central passage in which the driver shaft is rotatably disposed; and a release button disposed in the body and having at least a first position in which the driver shaft can be removed from the body and a second position in which the driver shaft cannot be removed from the body.

The instrument can include a preload assembly configured to bias the driver shaft in a distal direction relative to the body. In some embodiments, a location at which the preload assembly engages the driver shaft can be selected from amongst a plurality of locations to adjust the degree to which the driver shaft protrudes from the distal end of the body. The plurality of locations can be defined by radial projections that extend from the driver shaft. The instrument can include a guide sleeve positionable over a distal end of the body and configured to separate the body and the driver shaft from surrounding tissue when the instrument is used to drive a bone anchor assembly into bone. The sleeve can include a flared distal end and a flared proximal end. The sleeve can include a lever configured to pivot at a fulcrum point to selectively engage and disengage the sleeve with the body. The lever can be formed integrally with the sleeve at a living hinge. The sleeve can be rotatable with respect to the body and with respect to the driver shaft. The sleeve can be configured to engage any of a plurality of mating features spaced longitudinally along the body. The body can include an engagement portion formed at a distal end thereof, the engagement portion being configured to engage a corresponding engagement portion on a bone anchor assembly. The release button can be disposed in a housing portion of the body, the housing portion having a plurality of openings through which fluid can access the central passage. The release button can include a cylindrical recess in which a sliding collar is disposed, the driver shaft extending through the sliding collar. The sliding collar can include a plurality of openings spaced about a sidewall thereof. The instrument can include a preload spring disposed between the collar and the release button.

In some embodiments, an instrument for driving a bone anchor assembly into bone includes a driver shaft having a distal drive tip and a proximal driven end; an elongate body having proximal and distal ends that defines a central passage in which the driver shaft is rotatably disposed; a release button disposed in the body and having a collar slidably disposed therein, the collar being configured to selectively engage the driver shaft; and a preload spring disposed between the release button and the collar configured to bias the driver shaft in a distal direction with respect to the body.

The driver shaft can include a plurality of projections extending radially outward therefrom, and the degree to which the driver shaft protrudes from the distal end of the body can be adjusted by selecting which of the plurality of projections engages the collar.

In some embodiments, a method of driving a bone anchor assembly into bone includes engaging a drive interface of a bone anchor assembly with a drive tip of a driver shaft; advancing a body portion in which the driver shaft is rotatably disposed distally with respect to the bone anchor assembly to couple an engagement feature of the body portion with a corresponding engagement feature of the bone anchor assembly, wherein said distal advancement preloads a spring disposed in the body portion; rotating the driver shaft to drive the bone anchor assembly into bone; and actuating a release button to disengage the driver shaft from the body portion such that the driver shaft can be removed from the body portion.

The method can include positioning a guide sleeve disposed over the body portion between extension tabs of the bone anchor assembly and surrounding tissue. The method can include selecting from amongst a plurality of positions at which the driver shaft can be engaged by the body portion to adjust a degree to which the driver shaft protrudes from a distal end of the body portion.

The present invention further provides devices and methods as claimed.

BRIEF DESCRIPTION OF THE DRAWINGS

The invention will be more fully understood from the following detailed description taken in conjunction with the accompanying drawings, in which:

FIG. 2 is a perspective view of a driver instrument;

FIG. 3 is an exploded perspective view of the driver instrument of FIG. 2;

FIG. 4 is a sectional view of the driver instrument of FIG. 2;

FIG. 5 is an exploded perspective view of a body portion of the driver instrument of FIG. 2;

FIG. 6 is a sectional view of the body portion of the driver instrument of FIG. 2;

FIG. 7 is a perspective view of a release button of the driver instrument of FIG. 2;

FIG. 8 is a sectional view of the driver instrument of FIG. 2 with the release button in a released position;

FIG. 9 is a sectional view of the driver instrument of FIG. 2 with the release button in an engaged position;

FIG. 10 is a sectional view of the driver instrument of FIG. 2 coupled to a bone anchor assembly before a preload assembly is loaded;

FIG. 11 is a sectional view of the driver instrument of FIG. 2 coupled to a bone anchor assembly after the preload assembly is loaded;

FIG. 12 is a perspective view of a driver instrument;

FIG. 13 is an exploded perspective view of the driver instrument of FIG. 12; and FIG. 14 is a sectional view of the driver instrument of FIG. 12.

DETAILED DESCRIPTION

Driver instruments are disclosed herein with various features for improving usability, easing the task of cleaning or sterilizing the instrument, reducing patient trauma associated with use of the instrument, and/or reducing the cost and assembly burden of the instrument. For example, a driver instrument can include a guide sleeve to protect patient tissue from damage caused by rotating components of the instrument or a bone anchor assembly coupled thereto, and to protect extension tabs of the bone anchor assembly from inadvertent separation. By way of further example, an instrument can include a preload assembly for maintaining engagement of a driver shaft of the instrument with a bone anchor assembly. As yet another example, an instrument can consist of a small number of components which are configured for simple, tool-free assembly and disassembly. An instrument can also be configured for use with bone anchor assemblies with and without extension tabs.

Certain exemplary embodiments will now be described to provide an overall understanding of the principles of the structure, function, manufacture, and use of the devices and methods disclosed herein. One or more examples of these embodiments are illustrated in the accompanying drawings. Those of skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Prior Art Bone Anchor Assembly

Figure 1A:
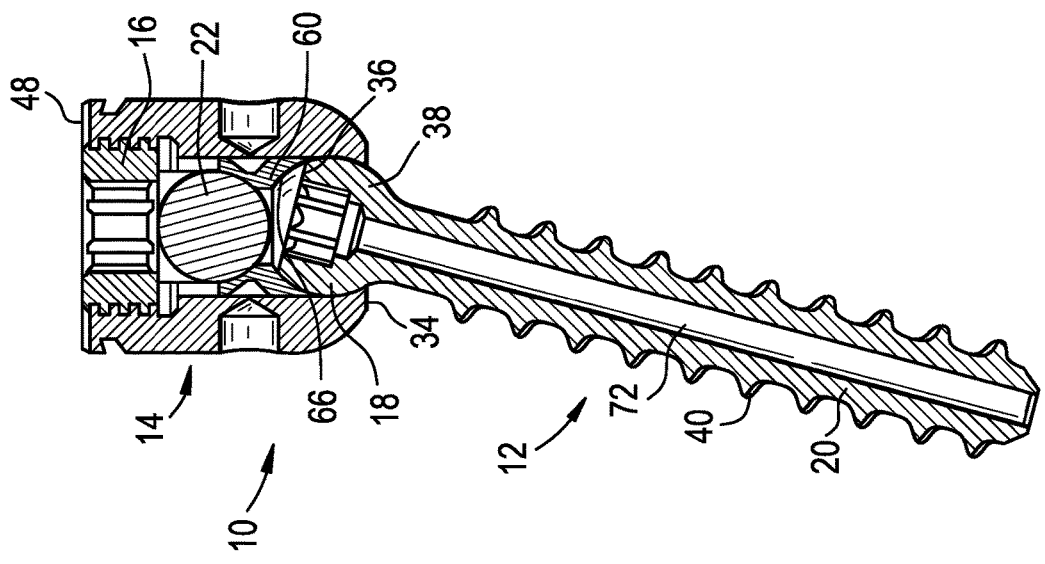
FIG. 1A is an exploded perspective view of a prior art bone anchor assembly.
Figure 1B:
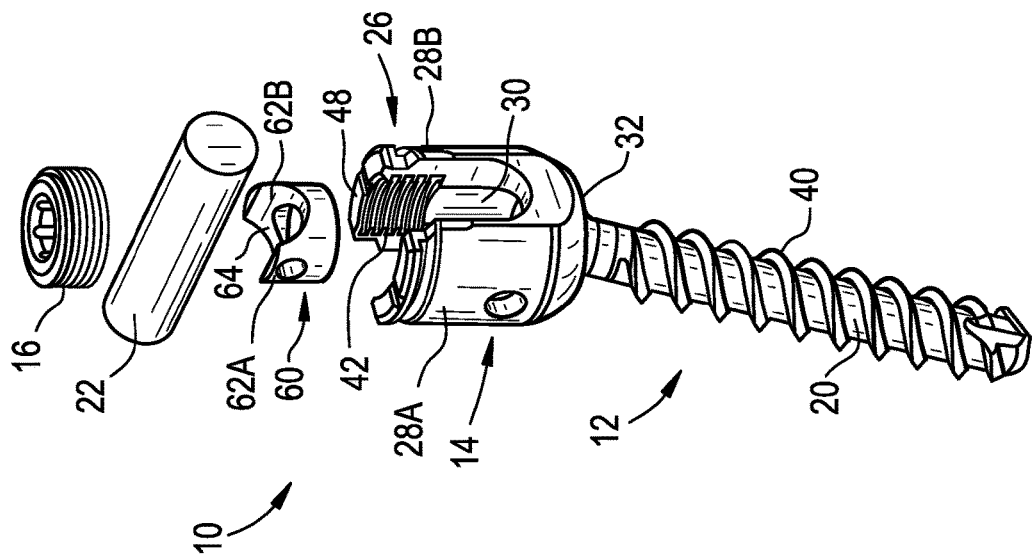
FIG. 1B is a sectional view of the prior art bone anchor assembly of FIG. 1A.

FIGS. 1A-1B illustrate a prior art bone anchor assembly 10 that includes a bone anchor 12, a receiver member 14 for receiving a spinal fixation element, such as a spinal rod 22, to be coupled to the bone anchor 12, and a closure mechanism 16 to capture a spinal fixation element within the receiver member 14 and fix the spinal fixation element with respect to the receiver member 14. The bone anchor 12 includes a proximal head 18 and a distal shaft 20 configured to engage bone. The receiver member 14 has a proximal end 26 having a pair of spaced apart arms 28A, 28B defining a recess 30 therebetween and a distal end 32 having a distal end surface 34 defining an opening through which at least a portion of the bone anchor 12 extends. The closure mechanism 16 can be positionable between and can engage the arms 28A, 28B to capture a spinal fixation element, e.g., a spinal rod 22, within the receiver member 14 and fix the spinal fixation element with respect to the receiver member 14.

The proximal head 18 of the bone anchor 12 is generally in the shape of a truncated sphere having a planar proximal surface 36 and an approximately spherically-shaped distal surface 38. The illustrated bone anchor assembly is a polyaxial bone screw designed for posterior implantation in the pedicle or lateral mass of a vertebra. The proximal head 18 of the bone anchor 12 engages the distal end 32 of the receiver member 14 in a ball and socket like arrangement in which the proximal head 18 and the distal shaft 20 can pivot relative to the receiver member 14. The distal surface 38 of the proximal head 18 of the bone anchor 12 and a mating surface within the distal end 32 of the receiver member 14 can have any shape that facilitates this arrangement, including, for example, spherical (as illustrated), toroidal, conical, frustoconical, and any combinations of these shapes.

The distal shaft 20 of the bone anchor 12 can be configured to engage bone and, in the illustrated embodiment, includes an external bone engaging thread 40. The thread form for the distal shaft 20, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Patent Application Publication No. 2013/0053901, filed on Aug. 22, 2012, both of which are hereby incorporated by reference herein. The distal shaft 20 can also include other structures for engaging bone, including a hook. The distal shaft 20 of the bone anchor 12 can be cannulated, having a central passage or cannula 72 extending the length of the bone anchor to facilitate delivery of the bone anchor over a guidewire in, for example, minimally-invasive procedures. Other components of the bone anchor assembly 10, including, for example, the closure mechanism 16, the receiver member 14, and the compression member 60 (discussed below) can be cannulated or otherwise have an opening to permit delivery over a guidewire. The distal shaft 20 can also include one or more sidewall openings or fenestrations that communicate with the cannula to permit bone in-growth or to permit the dispensing of bone cement or other materials through the bone anchor 12. The sidewall openings can extend radially from the cannula through the sidewall of the distal shaft 20. Exemplary systems for delivering bone cement to the bone anchor assembly 10 and alternative bone anchor configurations for facilitating cement delivery are described in U.S. Patent Application Publication No. 2010/0114174, filed on Oct. 29, 2009, which is hereby incorporated by reference herein. The distal shaft 20 of the bone anchor 12 can also be coated with materials to permit bone growth, such as, for example, hydroxyapatite, and the bone anchor assembly 10 can be coated partially or entirely with anti-infective materials, such as, for example, tryclosan.

The proximal end 26 of the receiver member 14 includes a pair of spaced apart arms 28A, 28B defining a U-shaped recess 30 therebetween for receiving a spinal fixation element, e.g., a spinal rod 22. Each of the arms 28A, 28B can extend from the distal end 32 of the receiver member 14 to a free end. The outer surfaces of each of the arms 28A, 28B can include a feature, such as a recess, dimple, notch, projection, or the like, to facilitate connection of the receiver member 14 to instruments. For example, the outer surface of each arm 28A, 28B can include an arcuate groove at the respective free end of the arms. Such grooves are described in more detail in U.S. Pat. No. 7,179,261, issued on Feb. 20, 2007, which is hereby incorporated by reference herein.

The distal end 32 of the receiver member 14 includes a distal end surface 34 which is generally annular in shape defining a circular opening through which at least a portion of the bone anchor 12 extends. For example, the distal shaft 20 of the bone anchor 12 can extend through the opening.

The bone anchor 12 can be selectively fixed relative to the receiver member 14. Prior to fixation, the bone anchor 12 is movable relative to the receiver member 14 within a cone of angulation generally defined by the geometry of the distal end 32 of the receiver member and the proximal head 18 of the bone anchor 12. The bone anchor 10 can be a favored angle screw, for example as disclosed in U.S. Pat. No. 6,974,460, issued on Dec. 13, 2005, and in U.S. Pat. No. 6,736,820, issued on May 18, 2004, both of which are hereby incorporated by reference herein. Alternatively, the bone anchor assembly can be a conventional (non-biased) polyaxial screw in which the bone anchor pivots in the same amount in every direction.

The spinal fixation element, e.g., the spinal rod 22, can either directly contact the proximal head 18 of the bone anchor 12 or can contact an intermediate element, e.g., a compression member 60. The compression member 60 can be positioned within the receiver member 14 and interposed between the spinal rod 22 and the proximal head 18 of the bone anchor 12 to compress the distal outer surface 38 of the proximal head 18 into direct, fixed engagement with the distal inner surface of the receiver member 14. The compression member 60 can include a pair of spaced apart arms 62A and 62B defining a U-shaped seat 64 for receiving the spinal rod 22 and a distal surface 66 for engaging the proximal head 18 of the bone anchor 12.

The proximal end 26 of the receiver member 14 can be configured to receive a closure mechanism 16 positionable between and engaging the arms 28A, 28B of the receiver member 14. The closure mechanism 16 can be configured to capture a spinal fixation element, e.g., a spinal rod 22, within the receiver member 14, to fix the spinal rod 22 relative to the receiver member 14, and to fix the bone anchor 12 relative to the receiver member 14. The closure mechanism 16 can be a single set screw having an outer thread for engaging an inner thread 42 provided on the arms 28A, 28B of the receiver member 14. In other embodiments, however, the closure mechanism 16 can include an outer set screw operable to act on the compression member 60 and an inner set screw operable to act on the rod 22. The receiver member 14 can include or can be coupled to one or more extension tabs (not shown) that extend proximally from the receiver member 14 to functionally extend the length of the arms 28A, 28B. The extension tabs can facilitate installation and assembly of a fixation or stabilization construct and can be removed prior to completing a surgical procedure.

The bone anchor assembly 10 can be used with a spinal fixation element such as rigid spinal rod 22. Alternatively, the spinal fixation element can be a dynamic stabilization member that allows controlled mobility between the instrumented vertebrae.

In use, the bone anchor assembly 10 can be assembled such that the distal shaft 20 extends through the opening in the distal end 32 of the receiver member 14 and the proximal head 18 of the bone anchor 12 is received in the distal end 32 of the receiver member 14. A driver instrument can be fitted with the bone anchor 12 to drive the bone anchor 12 into bone. The compression member 60 can be positioned within the receiver member 14 such that the arms 62A, 62B of the compression member are aligned with the arms 28A, 28B of the receiver member 14 and the lower surface of the compression member 14 is in contact with the proximal head 18 of the bone anchor 12. A spinal fixation element, e.g., the spinal rod 22, can be located in the recess 30 of the receiver member 14. The closure mechanism 16 can be engaged with the inner thread 42 provided on the arms 28A, 28B of the receiver member 14. A torsional force can be applied to the closure mechanism 16 to move it within the recess 30 so as to force the spinal rod 22 into engagement with the compression member 60 and to in turn force the compression member 60 onto the proximal head 18 of the bone anchor 12, thereby fixing the spinal rod 22 relative to the receiver member 14 and locking the angular position of the bone anchor 12 relative to the receiver member 14.

The driver instruments disclosed herein can be configured to operate in conjunction with bone anchor assemblies of the type described above or other types known in the art. Exemplary bone anchor assemblies include monoaxial screws, polyaxial screws, uniplanar screws, favored-angle screws, and/or any of a variety of other bone anchor types known in the art. Further information on favored-angle screws can be found in U.S. Patent Application Publication No. 2013/0096618, filed on Oct. 9, 2012, which is hereby incorporated by reference herein. Bone anchor assemblies are sometimes referred to herein simply as "bone anchors."

Driver Instruments and Related Methods

FIGS. 2-11 illustrate an exemplary embodiment of a driver instrument 200 for driving a bone anchor assembly. The driver instrument 200 can also be used to drive a bone tap or any other rotationally-driven element. The instrument 200 generally includes a driver shaft 202, a guide sleeve 204, and a body 206. The body 206 can define a central passage through which the driver shaft 202 is received and in which the driver shaft can rotate relative to the body. A distal portion of the body 206 can be received within a central passage of the guide sleeve 204 such that the body is rotatable with respect to the guide sleeve.

As shown in FIG. 3, the driver shaft 202 can include an elongate cylindrical body having a proximal end 202p and a distal end 202d and extending along a central longitudinal axis L1. The body of the driver shaft 202 can be cannulated to allow passage of a guidewire therethrough. The cannulation can also allow for injection of bone cement or other flowable materials through the driver shaft 202 to a bone anchor assembly coupled thereto.

The proximal end 202p of the driver shaft 202 can include a modular coupling 208 for selectively attaching the driver shaft to a structure or device for applying a rotational force to the driver shaft about the longitudinal axis L1. For example, the modular coupling 208 can be configured to attach the driver shaft 202 to a handle or knob configured to be grasped by a user, to a powered device such as an electric or pneumatic drill or driver, or to a surgical robot. In other embodiments, the driver shaft 202 can include a handle formed integrally therewith.

The distal end 202d of the driver shaft 202 can include a drive tip 210 for engaging a corresponding drive interface of a bone anchor and for transferring rotational force applied to the driver shaft to the bone anchor. Exemplary drive tips include Phillips, slotted, hexalobe, Torx®, hexagonal, pentalobe, and the like, of various standard or non-standard sizes. The drive tip 210 can also include a modular connector such that any of a plurality of drive tips having different types or sizes can be selectively coupled to the distal end of the driver shaft 202.

The driver shaft 202 can also include one or more radial projections or protrusions to facilitate interaction with various components of the body 206, as detailed below. In the illustrated embodiment, the driver shaft 202 includes proximal and distal radial projections 212, 214. The proximal projection 212 can include proximal-facing and distal-facing surfaces that extend substantially perpendicular to the driver shaft 202. The distal projection 214 can include a proximal-facing surface that is substantially perpendicular to the driver shaft 202 and a distal-facing surface that extends from the driver shaft at an oblique angle.

As shown in FIGS. 3-4, the guide sleeve 204 can include an elongate tubular frame having a proximal end 204p and a distal end 204d and extending along a central longitudinal axis L2. One or both ends of the sleeve 204 can be flared or enlarged such that the end has a diameter greater than that of the central portion of the sleeve. For example, the sleeve 204 can have a flared proximal portion 216 sized to accommodate a corresponding flared portion of the body 206. The flared proximal portion 216 can provide an indication to a user as to the proper orientation of the sleeve 204 with respect to the body 204 during assembly of the instrument 200. By way of further example, the sleeve 204 can have a flared distal portion 218 to guide or facilitate insertion of at least a portion of a bone anchor assembly therein. In other words, the flared distal portion 218 can act as a funnel or lead-in for the proximal end of a bone anchor assembly as it is inserted into the distal end of the sleeve 204.

The sleeve 204 can also include one or more mating features for coupling the sleeve to the body 206. In the illustrated embodiment, the mating features include first and second tabs or projections 220 that extend radially-inward towards the central axis L2 of the sleeve 204. The tabs 220 can be configured to engage corresponding grooves, recesses, or other mating features formed on the body, as discussed further below. The tabs 220 can extend from respective lever arms 222 which can be pivoted with respect to the sleeve 204 to move the tabs radially inward towards the central passage of the sleeve or radially outward away from the central passage of the sleeve. A leading proximal edge of the tabs 220 can be chamfered to allow the tabs to cam over the exterior of the body 206 until they snap into a recess or groove formed in the body.

Each lever arm 222 can be a separate component from the sleeve 204, or can be formed integrally with the sidewall of the sleeve as shown, e.g., by removing material from the sleeve to define an outline of the lever arm. A small section of material can be left on each lateral side of the lever arm 222 to define a living hinge 224 that acts as a fulcrum for the lever arm. While removal of material from the sleeve 204 is generally described herein, it will be appreciated that the lever arms 222 can be formed by addition of material to the sleeve, by molding, or by other processes which will be apparent to one skilled in the art. A portion of the lever arm 222 disposed opposite the fulcrum 224 from the portion of the lever arm from which the tab 220 extends can serve as a button 226 which, when depressed by a user, causes the tab to move radially outward and disengage the body 206. The material used to form the fulcrum 224 can have resilient properties such that, when the button portion 226 of the lever arm 222 is released by the user, the tabs 220 can be biased radially inward back towards a position in which they engage the body 206. Other biasing elements, such as coiled or leaf springs, can be included instead or in addition.

As shown in FIG. 5, the body 204 can extend along a central longitudinal axis L3 and can include a distal stem portion 228 and a proximal housing 230 in which a release button and preload assembly are disposed. The stem portion 228 and the proximal housing 230 can collectively define a continuous passage 232 (shown in FIG. 6) through the body 206 in which the driver shaft 202 can be received. Depending on the operating configuration of the instrument 200, the driver shaft 202 can be configured to rotate and/or translate longitudinally in various directions within the passage 232. The stem portion 228 of the body 206 can be sized and configured to be received within the central passage of the sleeve 204. When the instrument is fully-assembled, the central longitudinal axis L1 of the driver shaft 202 can be collinear with the central longitudinal axis L2 of the sleeve 204 and the central longitudinal axis L3 of the body 206.

The distal tip of the stem portion 228 can include an engagement feature configured to engage at least a portion of a bone anchor assembly. For example, the distal tip can include an external thread 234 as shown that is sized and configured to engage a corresponding internal thread formed in the receiver member of a bone anchor assembly, or an internal thread formed in one or more extension tabs or tubes extending proximally from the receiver member. It will be appreciated that various other engagement features can be used instead or in addition.

The stem portion 228 can include one or more protrusions, bulges, or other areas of increased diameter 236 configured to support the extension tabs of a bone anchor assembly when the distal tip is engaged with the bone anchor assembly. Such protrusions 236 can help prevent the extension tabs from bending inward towards the body 206 and breaking off or separating from the bone anchor assembly prematurely.

The proximal end of the stem portion 228 can include one or more mating features to which the sleeve 204 can be coupled. In the illustrated embodiment, the stem portion 228 includes first and second grooves 238, 240 that extend entirely around the outer circumference of the stem portion. It will be appreciated, however, that any number of mating features of various types can be used instead or in addition. The first and second grooves 238, 240 can be sized to receive the tabs 220 of the sleeve 204 therein to maintain the sleeve and the body 206 at a fixed longitudinal position with respect to one another while permitting the sleeve and the body to rotate with respect to one another. The longitudinal position of the sleeve 204 relative to the body 206 can be adjusted by changing which of the grooves 238, 240 is engaged by the tabs 220. For example, when the tabs 220 are disposed in the first groove 238, the distal end of the sleeve 204 can extend down over the receiver member of a bone anchor assembly coupled to the body 206. When the tabs 220 are disposed in the second groove 240, the distal end of the sleeve 204 can be retracted, e.g., such that the mating interface between the body 206 and the bone anchor assembly is disposed outside of the sleeve and able to be visualized or handled by a user. Different grooves can also be selected depending on the type of bone anchor assembly being used with the driver instrument 200 (e.g., based on whether or not the bone anchor assembly includes extension tabs).

The mating features 238, 240 can be formed at any longitudinal position along the body, however in the illustrated embodiment they are formed in a flared proximal portion 242. The flared proximal portion 242 has an outside diameter that is greater than the outside diameter of the distal portion of the stem 228 such that the flared portion corresponds to the flared portion 216 of the sleeve 204.

The proximal housing 230 of the body 206 can include a release button 244 with a corresponding button spring 246 and a locking pin 248. The housing 230 can also include a preload assembly. In the illustrated embodiment, the preload assembly includes a sliding collar 250 and a preload spring 252.

The housing 230 can define a chamber 254 that is open to a sidewall of the housing and that intersects with the central passage 232 of the body 206. The chamber 254 can be sized and shaped to correspond to the size and shape of the release button 244, and to slidably receive the release button therein such that the release button can move within the chamber towards and away from the central passage 232. One or more openings 256 can be formed in the sidewall of the housing 230, which can advantageously allow sterilizing solutions, cleaning agents, or other flowable materials to access the interior of the housing. In the illustrated embodiment, the housing 230 includes a faceted sidewall, with each face including at least one opening 256 formed therein. In addition, the proximal end surface 258 of the housing 230 can be completely open to allow further access to the interior of the housing. The housing 230 can also include one or more longitudinal grooves 260 to make the housing easier to grip.

The release button 244 can include a substantially rectangular-parallelepiped body having proximal and distal surfaces 244p, 244d. A cylindrical opening 262 can be formed through the button 244, extending between the proximal and distal surfaces. As shown in FIG. 7, an annular flange 264 can extend inward into the cylindrical opening 262 to define a proximal seat for the preload spring 252.

The sliding collar 250 can include a substantially tubular body having a distal annular lip 266 that extends radially-outward from an exterior surface of the collar to define a distal seat for the preload spring 252. The outside diameter of the lip 266 can be equal to or slightly less than the inside diameter of the cylindrical opening 262 formed in the release button 244 to allow the collar 250 to be received within the release button and to slide longitudinally therein. As shown in FIG. 6, the preload spring 252 can be captured on either end between the proximal and distal seats 264, 266 and along a length thereof between the interior of the release button 244 and the exterior of the collar 250.

One or more openings 268 can be formed in the sidewall of the collar 250, which can advantageously allow sterilizing solutions, cleaning agents, or other flowable materials to access the interior of the collar. In the illustrated embodiment, the collar 250 includes a plurality of elongated openings 268 spaced evenly about the circumference of the collar.

The button spring 246 can be partially received within a first bore 270 formed in the bottom of the chamber 254 and partially received within a second bore 272 formed in the sidewall of the release button 244 that faces the bottom of the chamber. The button spring 246 can thus be effective to bias the release button 244 away from the bottom of the chamber 254 such that the release button is urged in a direction radially-outward from the housing 230. The locking pin 248 can extend through an opening 274 formed in the sidewall of the housing 230 and into an elongated slot 276 formed in the release button 244. The locking pin 248 can thus limit the travel of the release button 244 within the chamber 254 to prevent the release button from falling out of the housing 230. The locking pin 248 can be welded or otherwise secured to the housing 230 after assembly to prevent inadvertent disassembly.

The release button 244 can be slidable within the chamber 254 between at least a first, released position (shown in FIG. 8) and a second, engaged position (shown in FIG. 9). The button 244 can be biased towards the engaged position and can be configured to move from the engaged position to the released position when depressed by a user.

In the released or disengaged position, as shown in FIG. 8, depression of the button 244 moves the collar 250 out of the path of the projections 212, 214 formed on the driver shaft 202, such that the collar does not engage the projections and such that the collar does not restrict longitudinal movement of the driver shaft relative to the body 206. Thus, in the disengaged position, the driver shaft 202 can be indexed to a desired longitudinal position with respect to the body 206, withdrawn completely from the body, or inserted through the body to assemble the instrument 200. The driver shaft 202 can be free to rotate relative to the body 206 when the button 244 is in the released position.

In the engaged position, as shown in FIG. 9, the bias of the button spring 246 urges the release button 244 upwards such that a portion of the sidewall of the sliding collar 250 interferes with at least one of the projections 212, 214 of the driver shaft 202 to prevent certain longitudinal movement of the driver shaft relative to the body 206. For example, in the engaged position, proximal movement of the driver shaft 202 relative to the body 206 is resisted by the bias of the preload spring 252 and eventually prevented altogether when the preload spring is completely compressed. The driver shaft 202 can remain free to rotate relative to the body 206 when the button 244 is in the engaged position. The driver shaft 202 can also be free to translate distally relative to the body 206 when the button 244 is in the engaged position, e.g., until one of the projections 214 of the driver shaft 202 hits a stop shoulder 278 formed in the distal stem portion 228 of the body 206.

Operation of the preload assembly is illustrated further in FIGS. 10-11. When the release button 244 is in the engaged position, longitudinal movement of the body 206 in a distal direction relative to the driver shaft 202 forces the sliding collar 250 to move proximally with respect to the release button 244, compressing the preload spring 252. In other words, as shown in FIG. 10, the preload spring 252 biases the sliding collar 250 (and the driver shaft 202 when the release button 244 is in the engaged position) distally with respect to the body 206. As the driver instrument 200 is advanced towards a bone anchor assembly 300, the distal end 202d of the driver shaft 202 comes into contact with the drive interface 302 of the bone anchor assembly, preventing further distal movement of the driver shaft.

Continued distal advancement of the instrument 200 towards the bone anchor assembly 300 causes the driver shaft 202 to slide proximally relative to the body 206, compressing the preload spring 252. As shown in FIG. 11, the relative longitudinal positions of the driver shaft 202 and the body 206 can be indexed by the placement of the protrusions 212, 214 such that, as the distal end 234 of the body 206 begins to threadably engage the receiver member 304 or extension tabs 306 of the bone anchor assembly 300, the driver shaft 202 contacts the drive interface 302 of the bone anchor assembly and begins to move proximally and compress the preload spring 252. This preload feature can advantageously maintain engagement between the driver shaft 202 and the bone anchor assembly 300. In particular, the preload function can maintain the driver shaft 202 in engagement with the drive interface 302 of the bone anchor assembly 300, preventing the driver shaft 202 from slipping out of engagement as the body 206 is advanced distally with respect to the bone anchor assembly.

The locations along the length of the driver shaft 202 at which the protrusions 212, 214 are positioned can be selected such that each protrusion corresponds to a different bone anchor configuration. In the illustrated embodiment, the proximal protrusion 212 can be used as the operative protrusion when a bone anchor assembly having extension tabs is used, such that the proximal protrusion is positioned just distal to the collar 250. On the other hand, when a bone screw assembly without extension tabs is used, the distal protrusion 214 can be used as the operative protrusion, such that the distal protrusion is positioned just distal to the collar 250 (e.g., such that the collar is disposed between the proximal and distal protrusions 212, 214).

In use, the instrument 200 can be provided initially in a completely assembled or completely disassembled state. The instrument 200 can also be provided initially in a partially-assembled state (e.g., with the preload assembly and release button 244 assembled to the body 206, but the body not yet assembled with the driver shaft 202 and/or the sleeve 204).

The driver shaft 202 can be inserted through the central passage 232 of the body 206 and the distal tip 202d of the driver shaft 202 can be engaged with a drive interface of a bone anchor assembly. The release button 244 can be depressed by the user to hold the button in the released position if necessary to allow insertion of the driver shaft 202 through the body 206. As the driver shaft 202 is inserted, the user can select the appropriate protrusion 212, 214 of the driver shaft to engage with the sliding collar 250, depending on the configuration of the bone anchor assembly (e.g., depending on whether or not the bone anchor assembly includes extension tabs).

With the driver shaft 202 inserted through the body 206, the body can be coupled to the receiver member or extension tabs of a bone anchor assembly, for example by threading the distal mating feature 234 of the body into corresponding threads of the bone anchor assembly. In the process of coupling the bone anchor assembly to the body 206, the body can be advanced distally relative to the driver shaft 202, which can be prevented from itself advancing distally by the drive interface of the bone anchor assembly. As the body 206 is advanced distally, the preload spring 252 can be compressed to generate a preload force that tends to maintain the driver shaft 202 in contact with the bone anchor assembly.

While the driver shaft 202 is preferably inserted through the body 206 prior to coupling the body to the bone anchor assembly (or when the body is only partially coupled to the bone anchor assembly) so as to preload the driver shaft, it will be appreciated that other assembly sequences are also possible.

Before or after coupling the body 206 to the bone anchor assembly and before or after inserting the driver shaft 202 through the body to engage the bone anchor assembly, the guide sleeve 204 can be assembled over the distal stem 228 of the body. A user can squeeze the button portions 226 of the lever arms 222 together to move the tabs 220 out of the central passage of the sleeve 204, slide the sleeve to the desired longitudinal position along the stem 228, and then release the buttons to allow the tabs to engage one of the grooves 238, 240 in the stem. The sleeve 204 can also be assembled without squeezing the buttons 226, instead simply allowing the tabs 220 to cam over the exterior of the stem 228 until they snap into the desired groove. It will be appreciated that the sleeve 204 need not necessarily be used when driving the bone anchor assembly. Use of the sleeve 204, however, can provide a number of advantages. For example, the sleeve 204 can form a protective barrier between patient tissue and components which may rotate during screw installation, such as the extension tabs, the receiver member, or the driver shaft 202. This can desirably prevent delicate tissue (e.g., muscle, nerves, vasculature, connective tissue, etc.) from being abraded, cut, tangled, or otherwise damaged by the rotating components.

With the instrument 200 assembled, the bone anchor assembly can be driven into bone by rotating the driver shaft 202 about the longitudinal axis L1, e.g., using manual force applied to a knob of the driver shaft or using a powered drill coupled to the driver shaft. As the bone anchor assembly advances into the bone, the driver shaft 202 can advance distally relative to the body 206, gradually unloading the preload spring 252. In some embodiments, the distal protrusion 214 can be positioned such that it contacts the shoulder 278 formed in the central passage 232 of the body 206 to prevent over-advancement of the driver shaft 202.

When the bone anchor assembly is implanted to the target depth, or at any other time desired by a user, the instrument 200 can be decoupled from the bone anchor assembly. For example, the body 206 can be detached from the bone anchor assembly by unthreading the body from the extension tabs (or from the receiver member). As another example, the driver shaft 202 can be detached from the bone anchor assembly by pushing the release button 244 to move the collar 250 to the released position and withdrawing the driver shaft proximally relative to the body 206.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present invention. It will further be appreciated that the instrument 200 can be used in a similar manner to remove a bone anchor assembly previously implanted or partially implanted in bone.

As evident from the foregoing, in at least some embodiments, the instrument 200 can provide one or more advantages as compared with other driver instruments:

The instrument 200 can be quickly assembled or disassembled by simple button pushes without requiring tools or complex procedures.

The ability to rapidly assemble and disassemble the instrument 200 can facilitate more effective, more comprehensive, and/or more expedient cleaning, sterilization, and reuse of the instrument.

The guide sleeve 204 can protect adjacent tissue from being injured or destroyed by rotating components of the instrument 200 or bone anchor assembly.

The guide sleeve 204 can be a single piece design that reduces component quantity and facilitates more effective, more comprehensive, and/or more expedient cleaning, sterilization, and reuse of the instrument 200. The single piece design can also reduce the overall profile of the instrument 200 and thus allow bone anchor insertion through a smaller-diameter cannula.

The guide sleeve 204 can be completely removable from the instrument 200 to allow the instrument to be used without the guide sleeve.

The guide sleeve 204 can protect the extension tabs of a bone anchor assembly from inadvertent breakage or separation from the receiver member, for example when lateral forces are applied to the driver instrument 200 to adjust an angle of insertion.

The guide sleeve 204 can help maintain rigid alignment between the driver shaft 202 and the bone anchor assembly during insertion.

The openings 256 in the body housing 230 and the openings 268 in the sliding collar 250 can allow passage of cleaning solutions, sterilization fluids, and other flowable materials to facilitate more effective, more comprehensive, and/or more expedient cleaning, sterilization, and reuse of the instrument 200.

The openings 256 and grooves 260 in the body housing 230 can provide an enhanced gripping surface for the user. The openings 256 can also allow a crossbar to be inserted therethrough to create a T-shaped structure for applying additional torque through the body 206.

The guide sleeve 204 and driver shaft 202 can be positioned at different longitudinal locations along the body 206 to allow the instrument 200 to be used with bone anchor assemblies with and without extension tabs.

The driver shaft 202 can be completely removable from the instrument 200 to allow the driver shaft to be used without the remainder of the instrument (e.g., to fine tune the insertion depth of the bone anchor assembly after initial placement).

The instrument 200 can provide a preload function to maintain contact between the driver shaft 202 and the bone anchor assembly during insertion or removal.

FIGS. 12-14 illustrate another exemplary embodiment of a driver instrument 400. Except as indicated below and as will be readily apparent to one having ordinary skill in the art, the structure and operation of the driver instrument 400 is substantially similar to that of the driver instrument 200, and therefore a detailed description is omitted here for the sake of brevity. The driver instrument 400 can include a guide sleeve 404 with lever arms 422 oriented in a direction opposite to that of the guide sleeve 204 described above. In particular, the lever arms 422 can be oriented such that the tabs 420 configured to engage the body 406 are disposed at a distal end of the lever arms. The groove(s) 438 formed in the body 406 in which the tabs 420 are received can likewise be formed more towards the distal end of the stem portion 428. The driver instrument 400 can also omit the preload assembly, which can reduce the complexity and cost of the instrument. As shown, the release button 444 is configured to engage the driver shaft 402 directly, with the collar and preload spring being omitted.

The instruments disclosed herein can be constructed from any of a variety of known materials. Exemplary materials include those which are suitable for use in surgical applications, including metals such as stainless steel, polymers such as PEEK, ceramics, carbon fiber, and so forth. The various components of the instruments disclosed herein can be rigid or flexible. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers. The devices disclosed herein can also be compatible with image-guide surgical systems and with stimulation systems (e.g., neuromonitoring systems typically used to monitor for pedicle breach and to confirm screw or instrument placement).

The devices and methods disclosed herein can be used in minimally-invasive surgery and/or open surgery. While the devices and methods disclosed herein are generally described in the context of advancing a bone anchor assembly into a bone such as the pedicle or lateral mass of a human spine, it will be appreciated that the methods and devices disclosed herein can be used with any human or animal bone, implant, non-living object, and so forth.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. An instrument for driving a bone anchor assembly into bone, the instrument comprising:
    a driver shaft having a distal drive tip and a proximal driven end;
    an elongate body having proximal and distal ends that define a central passage in which the driver shaft is rotatably disposed, a proximal portion of the elongate body having a faceted sidewall that includes a plurality of throughholes formed in a single face of the faceted sidewall; and
    a release button disposed in one of the plurality of throughholes of the body and having at least a first position in which the driver shaft can be completely removed from the body and a second position in which the driver shaft cannot be removed from the body;
    wherein the release button prevents complete removal of the driver shaft from a proximal-most end of the elongate body when the release button is in the second position; and
    wherein the release button moves relative to the driver shaft to make the driver shaft completely removable from the proximal-most end of the elongate body when the release button is in the first position.

2. The instrument of claim 1, further comprising a preload assembly configured to bias the driver shaft in a distal direction relative to the body.

3. The instrument of claim 2, wherein a location at which the preload assembly engages the driver shaft can be selected from amongst a plurality of locations to adjust the degree to which the driver shaft protrudes from the distal end of the body.

4. The instrument of claim 3, wherein the plurality of locations are defined by radial projections that extend from the driver shaft.

5. The instrument of claim 2, wherein the preload assembly is coupled directly to the release button.

6. The instrument of claim 1, further comprising a guide sleeve positionable over the distal end of the body and configured to separate the body and the driver shaft from surrounding tissue when the instrument is used to drive the bone anchor assembly into the bone.

7. The instrument of claim 6, wherein the sleeve has a flared distal end and a flared proximal end.

8. The instrument of claim 6, wherein the sleeve includes a lever configured to pivot at a fulcrum point to selectively engage and disengage the sleeve with the body.

9. The instrument of claim 8, wherein the lever is formed integrally with the sleeve at a living hinge.

10. The instrument of claim 6, wherein the sleeve is rotatable with respect to the body and with respect to the driver shaft.

11. The instrument of claim 6, wherein the sleeve is configured to engage any of a plurality of mating features spaced longitudinally along the body.

12. The instrument of claim 1, wherein the body includes an engagement portion formed at a distal end thereof, the engagement portion being configured to engage a corresponding engagement portion on the bone anchor assembly.

13. The instrument of claim 1, wherein the plurality of throughholes allow fluid to access the central passage.

14. The instrument of claim 1, wherein the release button includes a cylindrical recess in which a sliding collar is disposed, the sliding collar being movable relative to the driver shaft.

15. The instrument of claim 14, wherein the sliding collar includes a plurality of openings spaced about a sidewall thereof.

16. The instrument of claim 14, further comprising a preload spring disposed between the collar and the release button.

17. The instrument of claim 16, wherein the preload spring is configured to move with the release button in a direction transverse to a longitudinal axis of the driver shaft.

18. The instrument of claim 14, wherein the sliding collar is configured to move with the release button in a direction transverse to a longitudinal axis of the driver shaft.

19. The instrument of claim 1, wherein the driver shaft can be removed from the proximal end of the body.

20. The instrument of claim 1, wherein the release button is configured to move in a direction transverse to a longitudinal axis of the driver shaft when transitioning from the first position to the second position.

21. The instrument of claim 1, wherein the release button is disposed distal to at least one of the plurality of throughholes.

22. An instrument for driving a bone anchor assembly into bone, the instrument comprising:
a driver shaft having a distal drive tip and a proximal driven end;
a monolithic elongate body having proximal and distal ends that define a central passage in which the driver shaft is rotatably disposed; and
a release button disposed in the body and having at least a first position in which the driver shaft can be removed from the body and a second position in which the driver shaft cannot be removed from the body;
wherein the elongate body includes a plurality of throughholes formed in a first face of a faceted sidewall of the elongate body, the release button being disposed distal to at least one of the plurality of throughholes.

23. The instrument of claim 22, wherein the elongate body includes at least one longitudinal groove formed between adjacent faces of the sidewall.

24. The instrument of claim 22, wherein a throughhole formed in a second face of the faceted sidewall is substantially aligned with one of the plurality of throughholes formed in the first face such that a crossbar can be passed through the throughholes of the first face and the second face to create a T-shaped structure for applying additional torque through the elongate body.

25. An instrument for driving a bone anchor assembly into bone, the instrument comprising:
a driver shaft having a distal drive tip and a proximal driven end;
an elongate body having proximal and distal ends that define a central passage in which the driver shaft is rotatably disposed; and
a release button disposed in the body and having at least a first activated position in which the driver shaft can be removed from the body and a second position in which the driver shaft cannot be removed from the body;
wherein the release button includes a cylindrical recess in which a sliding collar is disposed, the sliding collar being movable relative to the driver shaft;
wherein the sliding collar is configured to move with the release button in a direction transverse to a longitudinal axis of the driver shaft; and
wherein the driver shaft passes through the sliding collar, and the sliding collar prevents removal of the driver shaft when the release button is not activated.

* * * * *